US009205053B2

(12) United States Patent
Vogel et al.

(10) Patent No.: US 9,205,053 B2
(45) Date of Patent: *Dec. 8, 2015

(54) INJECTABLE MICROSPHERES FOR DERMAL AUGMENTATION AND TISSUE BULKING

(75) Inventors: Jean-Marie Vogel, Lincoln, MA (US); Richard Thomas, Lincoln, MA (US); Egisto Boschetti, Croissy-sur-Seine (FR)

(73) Assignee: Biosphere Medical, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/534,070

(22) Filed: Jul. 31, 2009

(65) Prior Publication Data

US 2011/0033508 A1    Feb. 10, 2011

Related U.S. Application Data

(63) Continuation of application No. 10/704,919, filed on Nov. 12, 2003, now abandoned, which is a continuation of application No. 09/528,991, filed on Mar. 20, 2000, now Pat. No. 6,660,301, which is a continuation-in-part of application No. 09/263,773, filed on Mar. 5, 1999, now Pat. No. 6,335,028.

(60) Provisional application No. 60/077,166, filed on Mar. 6, 1998.

(51) Int. Cl.
| | |
|---|---|
| *A61K 9/14* | (2006.01) |
| *A61K 9/00* | (2006.01) |
| *A61K 47/48* | (2006.01) |
| *A61K 49/04* | (2006.01) |
| *A61L 27/38* | (2006.01) |
| *A61L 27/50* | (2006.01) |
| *A61L 31/00* | (2006.01) |
| *A61L 31/14* | (2006.01) |
| *A61K 31/78* | (2006.01) |
| *A61K 31/785* | (2006.01) |
| *A61K 9/16* | (2006.01) |

(52) U.S. Cl.
CPC .............. *A61K 9/14* (2013.01); *A61K 9/0019* (2013.01); *A61K 9/1635* (2013.01); *A61K 9/1641* (2013.01); *A61K 31/78* (2013.01); *A61K 31/785* (2013.01); *A61K 47/48869* (2013.01); *A61K 47/48876* (2013.01); *A61K 49/048* (2013.01); *A61K 49/0442* (2013.01); *A61L 27/38* (2013.01); *A61L 27/50* (2013.01); *A61L 31/005* (2013.01); *A61L 31/14* (2013.01); *A61K 9/16* (2013.01); *A61L 2400/06* (2013.01)

(58) Field of Classification Search
CPC .................. A61K 9/0019; A61K 9/16
See application file for complete search history.

(56) References Cited

U.S. PATENT DOCUMENTS

| | | | |
|---|---|---|---|
| 3,223,083 A | | 12/1965 | Cobey |
| 3,900,378 A | * | 8/1975 | Yen et al. ............... 522/72 |
| 3,919,411 A | | 11/1975 | Glass |
| 4,192,784 A | | 3/1980 | Brown et al. |
| 4,197,846 A | | 4/1980 | Bucalo |
| 4,213,962 A | * | 7/1980 | Miura et al. ............ 424/78.27 |
| 4,413,070 A | | 11/1983 | Rembaum |
| 4,452,916 A | | 6/1984 | Boschetti |
| 4,500,658 A | | 2/1985 | Fox |
| 4,525,358 A | | 6/1985 | Baltes |
| 4,622,362 A | | 11/1986 | Rembaum |
| 4,786,555 A | | 11/1988 | Howard, Jr. |
| 4,803,075 A | | 2/1989 | Wallace |
| 4,955,635 A | | 9/1990 | Haraguchi |
| 4,956,350 A | * | 9/1990 | Mosbey ............... 514/55 |
| 4,999,188 A | | 3/1991 | Solodovnik et al. |
| 5,007,940 A | * | 4/1991 | Berg ................... 424/423 |
| 5,158,573 A | * | 10/1992 | Berg ................... 523/113 |
| 5,202,352 A | | 4/1993 | Okada et al. |
| 5,226,914 A | | 7/1993 | Caplan |
| 5,298,570 A | | 3/1994 | Tahara |
| 5,306,500 A | | 4/1994 | Rhee |
| 5,324,775 A | | 6/1994 | Rhee |
| 5,336,263 A | * | 8/1994 | Ersek et al. ............ 424/422 |
| 5,344,452 A | | 9/1994 | Lemperle |
| 5,358,502 A | * | 10/1994 | Herbig et al. ........... 604/892.1 |
| 5,451,406 A | | 9/1995 | Lawlin |

(Continued)

FOREIGN PATENT DOCUMENTS

| | | |
|---|---|---|
| EP | 0251695 A2 | 1/1988 |
| EP | 0648480 | 4/1995 |

(Continued)

OTHER PUBLICATIONS

Appell, "Injectables in the treatment of female stress incontinence", 1995, Current Opinion in Obstetrics and Gynecology, vol. 7, pp. 393-396.*

(Continued)

*Primary Examiner* — Ali Soroush

(74) *Attorney, Agent, or Firm* — Stoel Rives LLP

(57) ABSTRACT

The present invention relates to elastic, hydrophilic and substantially spherical microspheres useful for dermal augmentation and tissue bulking. The invention provides injectable compositions comprising the microspheres and a biocompatible carrier for use in dermal augmentation. The present invention further provides methods of dermal augmentation and tissue bulking, particularly for the treatment of skin contour deficiencies, Gastro-esophageal reflux disease, urinary incontinence, and urinary reflux disease, using the injectable compositions.

15 Claims, No Drawings

(56) References Cited

U.S. PATENT DOCUMENTS

| | | | |
|---|---|---|---|
| 5,470,911 A | 11/1995 | Rhee | |
| 5,550,187 A | 8/1996 | Rhee | |
| 5,550,188 A | 8/1996 | Rhee | |
| 5,578,709 A | 11/1996 | Woiszwillo | |
| 5,624,685 A | 4/1997 | Takahashi et al. | |
| 5,633,001 A | 5/1997 | Agerup | |
| 5,635,215 A | 6/1997 | Boschetti | |
| 5,648,100 A | 7/1997 | Boschetti | |
| 5,667,778 A | 9/1997 | Atala | |
| 5,670,177 A | 9/1997 | Briend et al. | |
| 5,695,480 A * | 12/1997 | Evans et al. | 604/264 |
| 5,716,404 A | 2/1998 | Vacanti | |
| 5,792,478 A | 8/1998 | Lawin | |
| 5,798,096 A | 8/1998 | Pavlyk | |
| 5,830,708 A | 11/1998 | Naughton | |
| 5,843,987 A | 12/1998 | Rajagopalan | |
| 5,855,610 A | 1/1999 | Vacanti | |
| 5,855,615 A | 1/1999 | Bley | |
| 5,885,829 A | 3/1999 | Mooney | |
| 5,906,934 A | 5/1999 | Grande | |
| 5,919,707 A | 7/1999 | Banks et al. | |
| 5,922,025 A | 7/1999 | Hubbard | |
| 5,981,825 A | 11/1999 | Brekke | |
| 5,992,025 A | 11/1999 | Fricke | |
| 6,086,863 A | 7/2000 | Ritter | |
| 6,214,331 B1 | 4/2001 | Vanderhoff | |
| 6,224,893 B1 | 5/2001 | Langer et al. | |
| 6,238,355 B1 | 5/2001 | Daum | |
| 6,335,028 B1 | 1/2002 | Vogel et al. | |
| 6,436,424 B1 | 8/2002 | Vogel | |
| 6,660,301 B1 | 12/2003 | Vogel | |
| 6,680,046 B1 | 1/2004 | Boschetti | |
| 6,790,456 B2 | 9/2004 | Vogel | |
| 6,911,219 B2 | 6/2005 | Matson | |
| 7,060,298 B2 | 6/2006 | Vogel | |
| 7,338,657 B2 | 3/2008 | Vogel | |
| 7,591,993 B2 | 9/2009 | Boschetti | |
| 8,142,815 B2 | 3/2012 | Vogel et al. | |
| 8,658,215 B2 | 2/2014 | Vogel et al. | |
| 2002/0068089 A1 | 6/2002 | Vogel et al. | |
| 2002/0187172 A1 | 12/2002 | Reb et al. | |
| 2003/0211083 A1 | 11/2003 | Vogel et al. | |
| 2003/0211165 A1 | 11/2003 | Vogel | |
| 2003/0212002 A1 | 11/2003 | Haskell-Luevano et al. | |
| 2004/0091425 A1 | 5/2004 | Boschetti | |
| 2004/0096514 A1 | 5/2004 | Vogel | |
| 2005/0025708 A1 | 2/2005 | Vogel | |
| 2005/0158393 A1 | 7/2005 | Reb | |
| 2006/0039896 A1 | 2/2006 | Kleinsek et al. | |
| 2006/0063732 A1 | 3/2006 | Vogel | |
| 2006/0251582 A1 | 11/2006 | Reb | |
| 2008/0033366 A1 | 2/2008 | Matson | |
| 2008/0039890 A1 | 2/2008 | Matson | |
| 2008/0118569 A1 | 5/2008 | Vogel | |
| 2008/0220077 A1 | 9/2008 | Vogel | |
| 2009/0117196 A1 | 5/2009 | Boschetti | |
| 2009/0186094 A1 | 7/2009 | Vogel | |
| 2010/0119572 A1 | 5/2010 | Boschetti | |
| 2011/0182998 A1 | 7/2011 | Reb | |

FOREIGN PATENT DOCUMENTS

| | | | |
|---|---|---|---|
| EP | 0648480 A2 | 4/1995 | |
| EP | 0713707 A1 | 5/1996 | |
| EP | 0811373 A2 | 12/1997 | |
| FR | 2.378.808 A1 | 8/1978 | |
| FR | 2784580 | 4/2000 | |
| GB | 2 144 327 A | 3/1985 | |
| JP | 6056676 | 3/1994 | |
| WO | WO 89/07455 A1 | 8/1989 | |
| WO | WO 92/06702 A1 | 4/1992 | |
| WO | WO 92/21327 | 12/1992 | |
| WO | WO-93/15721 | * 8/1993 | |
| WO | WO-94/21299 | * 9/1994 | |
| WO | WO 94/21299 | * 9/1994 | |
| WO | WO94/21299 | 9/1994 | |
| WO | WO 94/21299 A1 | 9/1994 | |
| WO | WO 96/12510 A1 | 5/1996 | |
| WO | WO 98/52543 | 11/1996 | |
| WO | WO 96/39464 | 12/1996 | |
| WO | WO 99/31167 | 6/1999 | |
| WO | WO 99/34829 | 7/1999 | |
| WO | WO 99/44643 | 9/1999 | |
| WO | WO 00/23054 | 4/2000 | |
| WO | WO 2010/062678 | 6/2010 | |

OTHER PUBLICATIONS

Jayakrishnan et al., Hydrogel microspheres from crosslinked poly(methyl methacrylate): synthesis and biocompatibility studies, Mar. 1989, Bull. Mater. Sci., vol. 12 No. 1, pp. 17-25.*

Lemperle et al. PMMA Microspheres for Intradermal Implantation: Part I. Animal Research, Jan. 1991, Annals of Plastic Surgery, vol. 26 No. 1, pp. 57-63.*

Stenberg et al., A New Bioimplant for the Endoscopic Treatment of Vesicuoureteral Reflux: Experimental and Short-Term Clinical Results, Aug. 1995, The Journal of Urology, vol. 154 iss. 2, pp. 800-803.*

Parulakar et al., Dextranomer dressing in the treatment of infected wound and cutaneous ulcers, 1985, Journal of Postgraduate Medicine, vol. 31 iss. 1, pp. 28-33.*

Shafik, "Intraesophageal polytef injection for the treatment of reflus esphagitis" Surgical Endoscopy 10:329-331 (1996).

Jiaqi, "A New Embolic Material: Super Absorbent Polymer (SAP) Microsphere and its Embolic Effects," *Nippon Acta Radiologica* 56(I):19-24 (1996) [Japanese].

Jiaqi, "A New Embolic Material: Super Absorbent Polymer (SAP) Microsphere and its Embolic Effects," *Nippon Acta Radiologica* 56(1):19-24 (1996) [English Translation].

U.S. Appl. No. 12/197,187 (U.S. Publ. No. 2009/0186094); Office Action Dated Feb. 2, 2011.

U.S. Appl. No. 13/014,172, filed Jan. 26, 2011, Reb et al.

U.S. Appl. No. 12/695,080, filed Jan. 27, 2010, Reb et al.

Beaujeux, "Trisacryl Gelatin Microspheres for Therapeutic Embolization, II: Preliminary Clinical Evaluation in Tumors and Arteriovenous Malformations" *AJNR* 17(3):541-548 (1996).

Berman, "Comparative Cost Analysis of Collagen Injection and Fascia Lata Sling Cystourethropexy for the Treatment of Type III Incontinence in Women," *J. Urology*, 157:122-124 (1997).

Boschetti, "Synthese et copolymerisation de nouveaux monomeres acryliques diiodes et triiodes," *Bull. Soc. Chim.Fr.*, 4:669-677 (1996) (with English Abstract).

Boschetti, "Polyacrylamide Derivatives to the Service of Bioseparations,"*J. Biochem-Biophys. Meth.*, 19:21-36 (1989).

Boschetti, Microspheres for Biochromatography and Biomedical Applications: Part I. Preparation of Microbeads In: Microspheres, Microencapsulation and Liposomes, John Wiley & Sons, Arshady R., Ed. 2: 171-189 (1999).

Brown, "Syntheses and copolymerizations of new water-soluble polyiodinated acrylic monomers," *Makromol. Chem., Rapid Commun.* 6:503-507 (1985).

Cherksey, "Adrenal Chromaffin Cells on Microcarriers Exhibit Enhanced Long-Term Functional Effects When Implanted into the Mammalian Brain," *IBRO*, 657-664 (1996).

Chowdhury., "Use of Microbeads for Cell Transplantation," In: Advanced Research on Animal Cell Technology, A.O.A. Miller ed., Kluwers Acad. Press, 315-327(1989).

Communication Pursuant to Article 96(2) EPC issued on Dec. 3, 2004 in connection with European Application No. 01922415.3.

Dixit, "Hepatocyte immobilization on pHEMA microcarriers and its biologically modified forms" *Cell Transplantation* 1:391-399 (1992).

Edgerton, "Indications for and Pitfalls of Soft Tissue Augmentation with Liquid Silicone" Plast. Reconstr. Surg., 58:157-163 (1976).

Eppley., "A Potential Biomaterial Composite for Dermal and Subcutaneous Augmentation," *Annals of Plastic Surgery*, 32(5):463-468 (1994).

(56) References Cited

OTHER PUBLICATIONS

Gerhart, "Biomechanical Optimization of a Model Particulate Composite for Orthopaedic Applications," *Journal of Orthopedic Research*, 4:76-85 (1986).
Glowacki, "Comparison of Multinucleated Cells Elicited in Rats by Particulate Bone, Polyethylene, or Polymethylmethacrylate," *Journal of Bone and Mineral Research*, 1(4):327-331 (1986).
Goldring, "Multinucleated Cells Elicited in Response to Implants of Devitalized Bone Particles Possess Receptors for Calcitonin," *Journal of Bone and Mineral Research*, 3(1):117-120 (1988).
Goodman, "The Effects of Bulk Versus Particulate Polymethylmethacrylate on Bone," *Clin. Orthop. Relat. Res.*, 232:255-262 (1988).
Herschorn, "Followup of Intraurethal Collagen for Female Stress Urinary Incontinence," *J. Urology*, 156:1305-1309 (1996).
Herzog, "Urinary Incontinence: Medical and Psychosocial Aspects," *Ann. Rev. Gerontol. Geriatrics*, 9(Chap. 3):74-119 (1989).
Horák, "Hydrogels in Endovascular Embolization. I. Spherical Particles of Poly(2-hydroethyl methacrylate) and Their Medico-biological Properties" *Biomaterials*, 7:188-192 (1986).
Horák, "Hydrogels in Endovascular Embolization. II. Clinical Use of Spherical Particles" *Biomaterials*, 7:467-470 (1986).
Horák, "Hydrogels in Endovascular Embolization. III. Radiopaque Spherical particles, Their Preparation and Properties" *Biomaterials*, 8:142-144 (1987).
Johnson, "Outcome of Respiratory Symptons After Anti-reflux Surgery on Patients With Gastroesphageal Reflux Disease," *Archives of Surgery*, 131:489-492 (1996).
Khullar, "GAX Collagen in the Treatment of Urinary Incontinence in Elderly Women: A Two Year Follow Up," *British J. Obstetrics & Gynecology*, 104:96-99 (1996).
Klutke, "Early Results With Antegrade Collagen Injection for Post-Radical Prostatectomy Stress Urinary Incontinence," *J. Urology*, 156:1703-1706 (1996).
Kondo, "Bladder Neck Support Prosthesis: A Nonoperative Treatment for Stress or Mixed Urinary Incontinence," *J. Urology*, 157:824-827 (1996).
Krukowski, "Charged Beads Stimulate Bone Formation" 34th Annual Meeting Orth. Res. Soc. (Feb. 1988).
Langer, "Tissue Engineering," *Science*, 260:920-926, May 14, 1993.
Laurent, "Trisacryl Gelatin Microspheres for Therapeutic Embolization, I: Development and In Vitro Evaluation," *Am. J. Neuroradiol.*, 17:533-540 (1996).
Laurent, "Etude Histologique de Plusieurs Materiaux D'Embolisation et D'Un Nouveau Type de Materiel Spherique et Adhesif," *Innov. Tech. Biol. Med. 10*: 358-366 (1989).
Laurent, "Etude Histologique de Plusieurs Materiaux D'Embolisation et D'Un Nouveau Type de Materiel Spherique et Adhesif," *Innov. Tech. Biol. Med. 10*: 358-366 (1989). (English-language Translation).
Leonard, "Treatment of Urinary Incontinence in Children by Endoscopically Directed Bladder Neck Injection of Collagen," *J. Urology*, 156:637-641 (1996).
Lemperle, "PMMA Microspheres for Intradermal Implantation: Part I. Animal Research," *Ann Plast Surg*, 26:57-63 (1991).
Lemperle, "PMMA-Microspheres (Artecoll) for Long-Lasting Correction of Wrinkles: Refinements and Statistical Results," *Aesthetic Plastic Surgery*, 22:356-365 (1998).
Lemperle, "Soft Tissue Augmentation with Artecoll: 10-Year History, Indications, Techniques, and Complications," *Dermatol Surg*, 29:573-587 (2003).
Levesque, "Ten-Year Experience With the Artificial Urinary Sphincter in Children," *J. Urology*, 156:625-628 (1996).
Levine, "Microcarrier Cell Culture: New Methods for Research-Scale Application," *Somatic Cell Genetics*, 3:149-155 (1977).
Lima, "Combined use of enterocystoplasty and a new type of artificial sphincter in the treatment of urinary incontinence," *J. Urology* 156:622-624 (1996).

Mazza, "Polymer Design in Dye Chromatography: From the definition of monomers to the evaluation of polymeric supports," in Protein-Dye Interactions: Developments and Applications, Vijayalakshmi M.A. ed., Elsevier Appl. Sciences, Elsevier Sci. Publ. Ltd., pp. 126-136 (1989).
McClelland, "Evaluation of Antibody Class in Response to Bovine Collagen Treatment in Patients With Urinary Incontinence," *J. Urology* 155:2068-2073 (1996).
Millikan, "Long Term Safety and Efficiency with Fibrel in the Treatment of Cutaneous Scars", *J Dermatol Surg Oncol*, 15:837-846 (1989).
Morhenn, "Phagocytosis of Different Particulate Dermal Filler Substances by Human Macrophages and Skin Cells," *Dermatol Surg*, 28:484-490 (2002).
Nebel. "Symptomatic Gastroesophageal Reflux: Incidence and Precipitating Factors," *Am. J. Dig. Dis.*, 21,(11):953-956 (1976).
Obrenovitch, "Microcarrier Culture of Fibroblastic Cells on Modified Trisacryl Beads," *Biol. Cell.*, 46:249-256 (1983).
Ott, "Biocompatibility of Microscopic Beads of PMMA (Polymethyl Methacrylate) in Rat Skin," Doctoral Dissertation, Johann Wolfgang Goethe University, Frankfurt am Main, Germany (41 pgs.) (1988).
Owen, "Marrow Stromal Stem Cells," *J Cell Sci, Suppl.*, 10:63-76, 1988.
Perez, "Submucosal Bladder Neck Injection of Bovine Dermal Collagen for Stress Urinary Incontinence in the Pediatric Population," *J. Urology*, 156:633-636 (1996).
Remacle, "Cultures of Preadipocytes on Microparticles Their Properties of Adhesion Proliferation and Differentation," *Manuscript from University Catholique de Louvain, Laboratiore de Biologie Cellulaire*, 1-33 (1997).
Reynolds, "Influence of pathophysiology, severity, and cost on the medical management of gastroesophageal reflux disease," *Am. J. Health-Sys. Pharm.* 53:S5-S12 (1996).
Stinson, "Tissue Reaction Induced in Guinea-Pigs by Particulate Polymethylmethacrylate, Polythene and Nylon of the Same Size Range," *British Jour. Exp. Pathology*, 46:135-146 (1964).
Tuncel, "Nonswellable and swellable ethylene glycol dimethacrylate-acrylic acid copolymer microspheres" *J. Polymer Sci.: Pt. A: Polymer Chem.* 34:45-55 (1996).
Van Wezel, "Growth of Cell-strains and Primary Cells on Microcarriers in Homogeneous Culture," *Nature*, 216:64-65 (1967).
Wein, "Pharmacology of Incontinence," *Urol. Clin. N. Am.*, 22:557-573 (1995).
U.S. Appl. No. 09/528,990; (U.S. Pat. No. 6,436,426) Office Action Dated Mar. 22, 2001.
U.S. Appl. No. 09/528,990; (U.S. Pat. No. 6,436,426) Office Action Dated Oct. 29, 2001.
U.S. Appl. No. 09/528,990; (U.S. Pat. No. 6.436,426) Interview Summary Dated Apr. 4, 2002.
U.S. Appl. No. 09/528,990; (U.S. Pat. No. 6,436,426) Notice of Allowability Dated Apr. 9, 2002.
U.S. Appl. No. 09/528,990; (U.S. Pat. No. 6,436,426) Supplemental Notice of Allowability Dated May 13, 2002.
U.S. Appl. No. 09/528,989; Office Action Dated Apr. 11, 2001.
U.S. Appl. No. 09/528,989; Office Action Dated Sep. 24, 2001.
U.S. Appl. No. 09/528,989; Office Action Dated Feb. 12, 2003.
U.S. Appl. No. 09/528,989; Office Action Dated Nov. 26, 2003.
U.S. Appl. No. 09/528,989; Notice of Allowability Dated Dec. 7, 2004.
U.S. Appl. No. 09/528,989; Office Action Dated Sep. 19, 2005.
U.S. Appl. No. 09/528,989; Office Action Dated Jan. 19, 2007.
U.S. Appl. No. 09/528,989; Office Action Dated Sep. 20, 2007.
U.S. Appl. No. 09/528,989; Office Action Dated Feb. 27, 2008.
U.S. Appl. No. 09/528,991; (U.S. Pat. No. 6,660,301) Office Action Dated Aug. 27, 2001.
U.S. Appl. No. 09/528,991; (U.S. Pat. No. 6,660,301) Office Action Dated May 21, 2002.
U.S. Appl. No. 09/528,991; (U.S. Pat. No. 6,660,301) Notice of Allowability Dated Jul. 2, 2003.
U.S. Appl. No. 10/220,984; (U.S. Pat. No. 7,338,657) Office Action Dated Aug. 24, 2005.
U.S. Appl. No. 10/220,984; (U.S. Pat. No. 7,338,657) Office Action Dated Apr. 18, 2006.

(56) References Cited

OTHER PUBLICATIONS

U.S. Appl. No. 10/220,984; (U.S. Pat. No. 7,338,657) Office Action Dated Jan. 10, 2007.
U.S. Appl. No. 10/220,984; (U.S. Pat. No. 7,338,657) Notice of Allowability Dated Oct. 18, 2007.
U.S. Appl. No. 10/029,294; (U.S. Pat. No. 7,060,298) Office Action Dated May 19, 2003.
U.S. Appl. No. 10/029,294; (U.S. Pat. No. 7,060,298) Office Action Dated Mar. 24, 2004.
U.S. Appl. No. 10/029,294; (U.S. Pat. No. 7,060,298) Office Action Dated Jan. 6, 2005.
U.S. Appl. No. 10/029,294; (U.S. Pat. No. 7,060,298) Office Action Dated Aug. 23, 2005.
U.S. Appl. No. 10/029,294; (U.S. Pat. No. 7,060,298) Notice of Allowability Dated Feb. 1, 2006.
U.S. Appl. No. 10/222,819; (U.S. Pat. No. 6,790,456) Notice of Allowability Dated May 6, 2004.
U.S. Appl. No. 10/704,919; (U.S. Publ. No. 2004/0096514) Office Action Dated Mar. 19, 2007.
U.S. Appl. No. 10/704,919; (U.S. Publ. No. 2004/0096514) Office Action Dated Jan. 9, 2008.
U.S. Appl. No. 10/704,919; (U.S. Publ. No. 2004/0096514) Office Action Dated May 14, 2008.
U.S. Appl. No. 10/704,919; (U.S. Publ. No. 2004/0096514) Office Action Dated Feb. 3, 2009.
U.S. Appl. No. 10/704,919; (U.S. Publ. No. 2004/0096514) Notice of Abandonment and Interview Summary Dated Feb. 3, 2009.
U.S. Appl. No. 10/919,257 (U.S. Publ. No. 2005/0025708) Office Action Dated Oct. 31, 2008.
U.S. Appl. No. 10/919,257 (U.S. Publ. No. 2005/0025708) Office Action Dated Aug. 4, 2009.
U.S. Appl. No. 10/919,257 (U.S. Publ. No. 2005/0025708) Office Action Dated Mar. 16, 2010.
U.S. Appl. No. 10/919,257 (U.S. Publ. No. 2005/0025708) Office Action Dated Oct. 1, 2010.
A.J. Wein, "Pharmacology of Incontinence," Urol. Clin. N. Am., 22:557-573 (1995).
Appell, "Injectables in the treatment of female stress incontinence" Curr. Opin. Obstetrics Gynecol., 7:393-396 (1995).
J. Chowdhury et al., "Use of Microbeads for Cell Transplantation," Advanced Research on Animal Cell Technology, pp. 315-327, 1989.
U.S. Appl. No. 12/009,181 (U.S. Publ. No. 2008/0118569); Office Action Dated Apr. 4, 2011.
Hori et al., 'A New Embolic Material: Super Absorbent Polymer (SAP) Microsphere and its Embolic Effects'. IVR, vol. 11, No. 3, pp. 75-81, 1996. With english abstract.
U.S. Appl. No. 08/150,148 (U.S. Pat. No. 5,635,215) Office Action Dated Nov. 30, 1995.
U.S. Appl. No. 08/150,148 (U.S. Pat. No. 5,635,215) Office Action Dated Jun. 3, 1996.
U.S. Appl. No. 08/150,148 (U.S. Pat. No. 5,635,215) Notice of Allowability Dated Sep. 20, 1996.
U.S. Appl. No. 08/471,303; (U.S. Pat. No. 5,648,100) Office Action Dated Oct. 16, 1995.
U.S. Appl. No. 08/471,303; (U.S. Pat. No. 5,648,100) Office Action Dated May 7, 1996.
U.S. Appl. No. 08/471,303; (U.S. Pat. No. 5,648,100) Notice of Allowability Dated Dec. 23, 1996.
U.S. Appl. No. 09/263,773; (U.S. Pat. No. 6,335,028) Office Action Dated Jul. 19, 2000.
U.S. Appl. No. 09/263,773; (U.S. Pat. No. 6,335,028) Office Action Dated Apr. 20, 2001.
U.S. Appl. No. 09/263,773; (U.S. Pat. No. 6,335,028) Notice of Allowability Dated Aug. 17, 2001.
U.S. Appl. No. 09/419,114; (U.S. Pat. No. 6,680,046) Office Action Dated Oct. 29, 2001.
U.S. Appl. No. 09/419,114; (U.S. Pat. No. 6,680,046) Office Action Dated Jul. 3, 2002.
U.S. Appl. No. 09/419,114; (U.S. Pat. No. 6,680,046) Notice of Allowability Dated Jul. 25, 2003.
U.S. Appl. No. 09/945,793; (U.S. Publ. No. 2002/0187172) Office Action Dated Jan. 29, 2003.
U.S. Appl. No. 09/945,793; (U.S. Publ. No. 2002/0187172) Office Action Dated Jul. 21, 2003.
U.S. Appl. No. 09/945,793; (U.S. Publ. No. 2002/0187172) Office Action Dated Apr. 29, 2004.
U.S. Appl. No. 10/133,177; (U.S. Pat. No. 6,911,219) Office Action Dated Aug. 2, 2004.
U.S. Appl. No. 10/133,177; (U.S. Pat. No. 6,911,219) Notice of Allowability Dated Feb. 18, 2005.
U.S. Appl. No. 10/220,982; (U.S. Publ. No. 2003/0211165) Office Action Dated Jul. 15, 2005.
U.S. Appl. No. 10/220,982; (U.S. Publ. No. 2003/0211165) Office Action Dated Jan. 20, 2006.
U.S. Appl. No. 10/220,982; (U.S. Publ. No. 2003/0211165) Office Action Dated Aug. 1, 2006.
U.S. Appl. No. 10/220,982; (U.S. Publ. No. 2003/0211165) Office Action Dated Jun. 11, 2007.
U.S. Appl. No. 10/220,982; (U.S. Publ. No. 2003/0211165) Office Action Dated Oct. 12, 2007.
U.S. Appl. No. 10/220,982; (U.S. Publ. No. 2003/0211165) Office Action Dated Mar. 21, 2008.
U.S. Appl. No. 10/220,982; (U.S. Publ. No. 2003/0211165) Office Action Dated Nov. 18, 2008.
U.S. Appl. No. 10/220,982; (U.S. Publ. No. 2003/0211165) Office Action Dated Aug. 13, 2009.
U.S. Appl. No. 10/220,982; (U.S. Publ. No. 2003/0211165) Office Action Dated Jan. 29, 2010.
U.S. Appl. No. 10/220,983; (U.S. Publ. No. 2003/0212022) Office Action Dated Mar. 18, 2004.
U.S. Appl. No. 10/220,983; (U.S. Publ. No. 2003/0212022) Office Action Dated Sep. 9, 2004.
U.S. Appl. No. 10/220,983; (U.S. Publ. No. 2003/0212022) Office Action Dated Mar. 9, 2005.
U.S. Appl. No. 10/692,785; (U.S. Publ. No. 2004/0091425) Office Action Dated Nov. 16, 2005.
U.S. Appl. No. 10/692,785; (U.S. Publ. No. 2004/0091425) Office Action Dated Jun. 2, 2006.
U.S. Appl. No. 10/692,785; (U.S. Publ. No. 2004/0091425) Office Action Dated Oct. 30, 2006.
U.S. Appl. No. 10/692,785; (U.S. Publ. No. 2004/0091425) Interview Summary Dated Nov. 21, 2006.
U.S. Appl. No. 10/692,785; (U.S. Publ. No. 2004/0091425) Office Action Dated Jul. 12, 2007.
U.S. Appl. No. 10/692,785; (U.S. Publ. No. 2004/0091425) Office Action Dated Jan. 24, 2008.
U.S. Appl. No. 10/692,785; (U.S. Publ. No. 2004/0091425) Office Action Dated Sep. 4, 2008.
U.S. Appl. No. 10/692,785; (U.S. Publ. No. 2004/0091425) Notice of Allowability Dated Sep. 29, 2008.
U.S. Appl. No. 11/030,182; Office Action Dated Nov. 18, 2005.
U.S. Appl. No. 11/030,182; Interview Summary Dated Jun. 29, 2006.
U.S. Appl. No. 11/253,435; (U.S. Publ. No. 2006/0063732) Office Action dated Apr. 6, 2007.
U.S. Appl. No. 11/253,435; (U.S. Publ. No. 2006/0063732) Office Action dated Feb. 26, 2008.
U.S. Appl. No. 11/253,435; (U.S. Publ. No. 2006/0063732) Office Action dated Nov. 18, 2008.
U.S. Appl. No. 11/253,435; (U.S. Publ. No. 2006/0063732) Office Action dated Sep. 14, 2009.
U.S. Appl. No. 11/253,435; (U.S. Publ. No. 2006/0063732) Office Action dated Apr. 8, 2010.
U.S. Appl. No. 11/430,789; (U.S. Publ. No. 2006/0251582) Office Action dated Jan. 23, 2008.
U.S. Appl. No. 11/430,789; (U.S. Publ. No. 2006/0251582) Office Action dated Sep. 12, 2008.
U.S. Appl. No. 11/430,789; (U.S. Publ. No. 2006/0251582) Office Action dated Aug. 17, 2009.
U.S. Appl. No. 11/430,789; (U.S. Publ. No. 2006/0251582) Office Action dated Apr. 14, 2010.
U.S. Appl. No. 11/669,127 (U.S. Publ. No. 2008/0039890); Office Action dated May 12, 2010.
Office Action dated Jun. 13, 2011 for U.S. Appl. No. 10/919,257.

(56) References Cited

OTHER PUBLICATIONS

Notice of Allowance dated Sep. 29, 2011 for U.S. Appl. No. 10/919,257.
Notice of Allowance dated Jan. 9, 2012 for U.S. Appl. No. 10/919,257.
Office Action dated Sep. 24, 2001 for U.S. Appl. No. 09/528,989.
Office Action dated Apr. 10, 2006 for U.S. Appl. No. 09/528,989.
Restriction Requirement dated Sep. 28, 2010 for U.S. Appl. No. 12/197,187.
Office Action dated Jun. 20, 2013 for U.S. Appl. No. 12/197,187.
Notice of Allowance dated Oct. 11, 2013 for U.S. Appl. No. 13/961,674.
Office Action dated Sep. 16, 2013 for U.S. Appl. No. 12/009,181.
Office Action dated Nov. 27, 2013 for U.S. Appl. No. 12/197,187.
Office Action dated Dec. 5, 2013 for U.S. Appl. No. 13/962,025.
Office Action dated Dec. 20, 2013 for U.S. Appl. No. 14/075,536.
Notice of Allowance dated Apr. 14, 2014 for U.S. Appl. No. 12/009,181.
Miyake et al., 'Sustained Decrease in Brain Regional Blood Flow After Micrisphere Embolism in Rats', Stroke 24:415-420, 1993.
Office Action dated Jun. 6, 2014 for U.S. Appl. No. 14/075,536.
Office Action dated Jun. 17, 2014 for U.S. Appl. No. 13/962,025.
Office action dated Sep. 22, 2014 for U.S. Appl. No. 12/197,187.
Notice of Allowance dated Nov. 4, 2014 for U.S. Appl. No. 13/962,025.
Office Action dated Dec. 3, 2014 for U.S. Appl. No. 14/075,536.
Dion et al., 'Dextran Microsphere Embolization: Experimental and Clinical Experience with Radiologic-Pathologic Correlation. Work in Process', RSNA Radiology, Sep. 1986.
Notice of Allowance dated Mar. 3, 2015 for U.S. Appl. No. 12/197,187.
Office Action dated Mar. 16, 2010 for U.S. Appl. No. 10/919,257.
Office Action dated Jun. 29, 2015 for U.S. Appl. No. 14/075,536.
Office Action dated Dec. 21, 2011 for U.S. Appl. No. 12/009,181.

* cited by examiner

INJECTABLE MICROSPHERES FOR DERMAL AUGMENTATION AND TISSUE BULKING

CROSS REFERENCE TO RELATED APPLICATIONS

This application is a continuation of U.S. Ser. No. 10/704,919 filed Nov. 12, 2003 (abandoned), which is a continuation of U.S. Ser. No. 09/528,991 filed Mar. 20, 2000 (now U.S. Pat. No. 6,660,301), which is a continuation-in-part U.S. Ser. No. 09/263,773; filed Mar. 5, 1999 (now U.S. Pat. No. 6,335,028), which claims the benefit of U.S. Provisional Ser. No. 60/077,166 filed Mar. 6, 1998, each of which is hereby incorporated by reference in its entirety.

FIELD

The present invention relates to dermal augmentation and tissue bulking, particularly for the treatment of gastroesophageal reflux disease, urinary incontinence, urinary reflux disease, or skin contour deficiencies and wrinkles, using injectable microspheres.

BACKGROUND

Gastroesophageal Reflux Disease ("GERD")

Although gastroesophageal reflux is a normal physiological phenomenon, in some cases it is a pathophysiological situation that can result in a variety of symptoms which may become severe in extreme cases. Gastro-Esophageal Reflux Disease ("GERD"), describes a backflow of acidic and enzymatic liquid from the stomach to the esophagus. It causes burning sensations behind the sternum that may be accompanied by regurgitation of gastric acid into the mouth or even the lung. Complications of GERD which define the severity of the disease include esophageal tissue erosion, and esophageal ulcer wherein normal epithelium is replaced by a pathological tissue.

Statistical data indicate that about 35% of the American population suffer from heartburn at least once a month and between 5 to 10% once a day. More importantly for this kind of disease about 2% of the American population suffer from GERD based on medical evidence data from endoscopic examination. This disease is related to the age of individuals and seems to increase after 40 years of age. (Nebel O. T. et al., *Am. J. Dig. Dis.*, 21(11):953-956 (1976)).

In normal patients, after a meal the lower esophageal sphincter remains closed, but in patients with GERD, it relaxes and allows some acidic material to reflux into the esophageal tube as a result of stomach contractions. Actually GERD can be attributed primarily to transient relaxation of the lower esophageal sphincter. In other cases, GERD can be attributed to decreased resting tone of the lower esophageal sphincter or to congenital small dimension of the sphincter itself. Other causes also exist which contribute to varying degrees to the existence and severity of this disease.

In addition, there are external factors that contribute to exacerbate the symptoms of GERD, which conditions include eating fatty foods, caffeine intake, smoking, tight clothing and certain medications. Decrease in salivation can also be a factor that exacerbates GERD, since under normal conditions saliva, which is an alkaline liquid, aids in neutralizing acidic reflux and therefore diminishing the duration of the acidic exposure of the esophagus.

Erythema is one of the first visible signs of GERD, which can be seen by endoscopy. Tissue erosion indicates more advanced disease which can then become deep ulcers and lead to cancer (adenocarcinoma increases in incidence faster than other types of cancer). Diffuse ulceration and specific complications occur in about 3.5% of patients less than 65 years of age with esophageal obstruction, blood loss, and in some cases, perforation. Ulcerative situations not only lead to complications, but they are also more resistant to treatments. Although severe complications are uncommon in young patients, they occur in about 20-30% of patients over 65 (Reynolds J. C, *Am. J. Health-Sys. Pharm* 53, (1996)).

Prior to the present invention, in an attempt to increase the function of the sphincter, bulking methods using bovine collagen and Teflon paste have been used in patients. Both methods have been unsuccessful, however, as these materials migrate over time from the initial site of implantation.

At present, GERD is generally managed by over-the-counter ("OTC") antacids or prescription drugs, including proton pump inhibitors, motility agents and $H_2$ blockers. In addition, a portion of GERD patients require surgical intervention; the most common type of surgery is fundoplication which can be done by conventional surgical techniques, or using laparoscopic techniques. However, fundoplication surgery carries the risk of serious side effects and is only marginally successful in curing GERD. Respiratory symptoms are also associated with GERD in about 50% of patients, and in patients undergoing fundoplication, these respiratory symptoms can even increase (76% reported in a study by Johnson W. E. et al., *Archives of Surgery*, 131:489-492 (1996)).

Urinary Incontinence and Urinary Reflux Disease

Urinary incontinence is a prevalent problem that affects people of all ages and levels of physical health, both in the community at large and in healthcare settings. Medically, urinary incontinence predisposes a patient to urinary tract infections, pressure ulcers, perineal rashes, and urosepsis. Socially and psychologically, urinary incontinence is associated with embarrassment, social stigmatization, depression, and especially for the elderly, an increased risk of institutionalization (Herzo et al., *Ann. Rev. Gerontol. Geriatrics*, 9:74 (1989)). Economically, the costs are astounding; in the United States alone, over ten billion dollars per year is spent managing incontinence.

Incontinence can be attributed to genuine urinary stress (urethra hypermobility), to intrinsic sphincter deficiency ("ISD"), or both. It is especially prevalent in women, and to a lesser extent incontinence is present in children (in particular, ISD), and in men following radical prostatectomy.

One approach for treatment of urinary incontinence involves administration of drugs with bladder relaxant properties, with anticholinergic medications representing the mainstay of such drugs. For example, anticholinergics such as propantheline bromide, and combination smooth muscle relaxant/anticholinergics such as racemic oxybutynin and dicyclomin, have been used to treat urge incontinence. (See, e.g., Wein A. J., *Urol. Clin. N. Am.*, 22:557 (1995)). Often, however, such drug therapies do not achieve complete success with all classes of incontinent patients, and often results in the patient experiencing significant side effects.

Besides drug therapies, other options used by the skilled artisan prior to the present invention include the use of artificial sphincters (Lima S. V. C. et al., *J. Urology*, 156:622-624 (1996), Levesque P. E. et al., *J. Urology*, 156:625-628 (1996)), bladder neck support prosthesis (Kondo A. et al., *J. Urology*, 157:824-827 (1996)), injection of crosslinked collagen (Berman C. J. et al., *J. Urology*, 157:122-124 (1997), Perez L. M. et al., *J. Urology,* 156:633-636 (1996); Leonard M. P. et al., *J. Urology,* 156:637-640 (1996)), and injection of polytetrafluoroethylene (Perez L. M. et al., *J. Urology,* 156: 633-636 (1996)).

A recent well known approach for the treatment of urinary incontinence associated with ISD is to subject the patient to periurethral endoscopic collagen injections. This augments the bladder muscle in an effort to reduce the likelihood of bladder leakage or stress incontinence.

Existing solutions to circumvent incontinence have well known drawbacks. The use of artificial sphincters for children with intractable incontinence requires long term surveillance of the urinary tract because of the potential for renal failure after device placement (Levesque P. E. et al., *J. Urology,* 156:625-628 (1996)). While endoscopically directed injections of collagen around the bladder neck has a quite high success rate in sphincter deficiency with no significant morbidity, the use of collagen can result in failures that occur after an average of two years and considerations need to be given to its cost effectiveness (Khullar V. et al., *British J. Obstetrics & Gynecology,* 104:96-99 (1996)). In addition, deterioration of patient continency, probably due to the migration phenomena (Perez L. M. et al.) may require repeated injections in order to restore continency (Herschorn S. et al., *J. Urology,* 156:1305-1309 (1996)).

The results with using collagen following radical prostatectomy for the treatment of stress urinary incontinence have also been generally disappointing (Klutke C. G. et al., *J. Urology,* 156:1703-1706 (1996)). Moreover, one study provides evidence that the injection of bovine dermal collagen produced specific antibodies of IgG and IgA class. (McCell and, M. and Delustro, F., *J. Urology* 155, 2068-2073 (1996)). Thus, possible patient sensitization to the collagen could be expected over the time.

Despite of the limited success rate, transurethral collagen injection therapy remains an acceptable treatment for intrinsic sphincter deficiency, due to the lack other suitable alternatives.

Urinary reflux disease, or "vesicoureteral reflux" in its medical term, simply means that urine goes backwards in the ureters during urination. The disease often occurs in young children. The ureter is the tube which connects the kidneys with the bladder. Urine is supposed to go in one direction: from the kidneys to the bladder. When urine goes up from the bladder to the kidneys, it can result in health problems for the person.

Urinary reflux can lead to kidney damage. Refluxing urine can carry bacteria to the kidney, where it can cause kidney infection. Children with reflux of urine are much more likely to have kidney infection than children who do not have reflux. The combination of reflux and infection can lead to areas of permanent kidney damage or "renal scarring." This scarring is detected by doing an X-ray called an intravenous pyelogram (IVP), or preferably, a renal scan. If it is extensive enough, the scarring can lead to loss of function of one or both kidneys.

The key to preventing renal scarring is preventing kidney infections. This is currently being carried out in two ways. In most cases, long term prophylactic antibiotics are given. The other method of preventing urinary tract infections is surgical correction of the reflux. Both methods, however, have drawbacks. Long term use of antibiotics may cause unpredictable side effects and surgical procedures involve unnecessary risks.

Even though many urinary reflux disease will go away on its own in children, some cases often lead to severe kidney and urinary tract infections and even total kidney failure. There is a need, therefore, for a safe, effective, less intrusive, and long lasting method of treating urinary reflux disease.

Skin Deficiencies

Damage to the skin due to aging, environmental exposure to the sun and other elements, weight loss, child bearing, disease such as acne and cancer, and surgery often results in skin contour deficiencies and other skin anomalies. In order to correct contour deficiencies and other anomalies of the skin, people often resort to cosmetic surgery, such as face lifts and skin tucks. Cosmetic surgery, however, has several drawbacks, in addition to the high cost associated with it. It is usually an invasive and risky procedure, having the potential of leaving scars in areas of operation and affecting normal biological and physiological functions. Furthermore, cosmetic surgery is often a limited option, available only for certain skin deficiencies.

In addition to cosmetic surgery, various other methods are used to remove or ameliorate the deficiencies with different levels of success. The use of injectable material for soft tissue augmentation is a method often used. The advantage of using hypodermic needles as a delivery device for dermal augmentation reflects the advantages of using hypodermic needles in general: easy, precise and, usually, non-invasive deliveries. Yet, the requirement for such use is also quite strict: the material to be delivered must be deliverable through the needles, which means the material must be able to easily pass through the hollow centers of the needles.

One method of dermal augmentation using injectable material is liquid or semi-liquid injections, usually containing collagen. The best known example is a collagen preparation manufactured by Collagen Corporation (now part of Inamed Corporation) and marketed by C. R. Bard. However, collagen is a naturally occurring substance which the body may enzymatically degrade and eliminate over time, thus requiring repeat treatments. Also, collagen may be displaced within the tissue in which it was originally injected, thereby reducing or eliminating the intended dermal augmentation effect. Collagen is also digested directly (biochemically), through macrophages, through the lymphatic system, or by other means. Even more alarming from a cosmetic perspective, collagen may move from the initial site of injection, causing unsightly bumps and bulges under the skin at undesired locations. See, e.g., Millikan, Long Term Safety and Efficacy with Fibrel in the Treatment of Cutaneous Scars, *J Dermatol Surg Oncol,* 15:837-846 (1989).

Injection of liquid silicone has also been used extensively to treat skin deficiencies. However, due to long term side effects, such as nodules, recurring cellulitis, and skin ulcers, the use of injectable silicone is on the decline. See, e.g., Edgerton et al., Indications for and pitfalls of soft tissue augmentation with liquid silicone, *Plast. Reconstr. Surg,* 58:157-163 (1976).

MicroParticles

Prior to the present invention, microspheres have been manufactured and marketed for in vitro use in anchorage dependent cell culture. (Van Vezel, A. L., *Nature,* 216:64-65 (1967); Levine et al., *Somatic Cell Genetics,* 3:149-155 (1977); Obrenovitch et al., *Biol. Cell.,* 46:249-256 (1983)). They have also been used in vivo to occlude blood vessels in the treatment of arteriovascular malformation, fistulas and tumors (See, U.S. Pat. No. 5,635,215, issued Jun. 3, 1997 to Boschetti et al.; Laurent et al., *J. Am. Soc. Neuroiol,* 17:533-540 (1996); and Beaujeux et al. *J. Am. Soc. Neuroial,* A:533-540 (1996)).

Further, direct implantation of cells into living tissues such as brain or liver to correct specific deficiencies has been attempted albeit with a number of failures. The major problems associated with direct cell transplantation are the long term viability of the cell transplant and the immunopathological as well as histological responses. Microparticles with cells attached on their surface have been used in some in vivo applications. Cherkesey et al., IBRO, 657-664 (1996), described the culture of adrenal cells on coated dextran beads and the implantation into mammalian brain to supplant some specific disorders related to 6-hydroxydopamine-induced unilateral lesions of the substantia nigra. The pre-attachment of cells to dextran microcarriers allowed for improved functions of the cells implanted into the brain. Also liver cells transplantation has been used to manage acute liver failure, or for the replacement of specific deficient functions such as conjugation of bilirubin or synthesis of albumin. For this purpose, an intrasplenic injection of hepatocytes grown on the surface of microspheres was performed (Roy Chowdhury et al., in: Advanced Research on Animal Cell Technology, AOA Miller ed., 315-327, Kluers Acad. Press, 1989).

Most of cell implant results have been, however, largely disappointing for the designated functions (or have had low levels of biological function).

Prior to the present invention, solid microparticles have also been used for the correction of skin deficiencies and for tissue bulking. For example, carbon particles, silicone particles, TEFLON (polytetrafluoroethylene) paste, collagen beads and polymethylmethacrylate spheres, have been used with disappointing results due to, inter alia, adverse tissue reactions, biological degradation and migration from the initial implantation location.

The problems associated with rigid and non-deformable particles, such as carbon particles and silicone particles, in tissue bulking or treating skin deficiencies are that they are either too fragile or too large to be injected, or too small and are digested or eliminated by the body. Therefore, such particles all have one or more of the following limitations: (i) too large to be injected through a 30 gauge or smaller needle; (ii) particles of irregular shape clump together, making injection difficult; (iii) particles are too fragile, resulting in breakage during injection and digestion of the residues; (iv) injected particles are too small and are digested by macrophages or other components of the lymphatic system; and (v) injected particles are displaced as they do not adhere to the surrounding cells.

Injectable deformable particles, such as TEFLON (polytetrafluoroethylene) particles, have also been used for tissue bulking and for treating skin deficiencies. However, TEFLON (polytetrafluoroethylene) particles have one or more of the following limitations: (1) the particles slide with the tissue and do not stay in place of injection; (2) the particles deform during and after injection, reducing the intended tissue bulking effect; and (3) the particles are digested or eliminated by the lymphatic system partly due to the fact that their diameters become smaller as a result of injection.

Therefore, there is a great need for safe, biocompatible, stable and effective methods of tissue bulking for the treatment of GERD, urinary incontinence, and urinary reflux disease and methods of dermal augmentation for treatment of skin disorders.

SUMMARY

The present invention encompasses the use of implantable microparticles, or microspheres or microbeads, in the treatment of GERD, urinary incontinence, urinary reflux disease and skin deficiencies such as skin wrinkles. In each use the particles are implanted into the appropriate tissue, muscle, organ etc. as a bulking or augmentation agent.

In a preferred embodiment, the invention provides a method of dermal augmentation, suitable for the treatment of skin deficiencies, and a method of tissue bulking, suitable for the treatment of GERD, urinary incontinence, or urinary reflux disease, wherein the microspheres used are injectable through needles of about 18 gauge or smaller, depending on the particular method and treatment, and are not capable of being digested or eliminated through the lymphatic or the immune system. Thus, the invention encompasses injectable compositions and methods for dermal augmentation or tissue bulking by injecting using syringes, catheters, needles or other means of injecting or infusing microspheres in a liquid medium so as to avoid surgical intervention.

The microparticles of the invention, whether implantable by injection or otherwise, are preferably pre-coated, with autologous cells, for example, muscle cells, fat cells and the like. The microparticles of the invention are biocompatible non-toxic polymers coated with, linked to or filled with cell adhesion promoters. The microparticles preferably contain a positive charge on their surface by way of a cationic monomer or polymer.

In one embodiment, the invention encompasses the treatment of gastroesophageal reflux disease in a human which comprises implanting hydrophilic biocompatible microparticles comprising (a) a positive charge and a cell adhesion promoter; and (b) autologous cells layered on the surface of said beads, into the lower esophageal sphincter. The microparticles are preferably microspheres or microbeads which are described in detail herein. The autologous cells are preferably taken from the area where the implantation is to be made. Serum or whole blood taken from the patient can be used to wash the microparticles prior to implantation. For GERD treatment, implantation is preferably made by using standard techniques known to the ordinary skilled artisan, such as injection (or injections) via syringe or other suitable devices.

In yet another embodiment, the invention encompasses the treatment of urinary incontinence in a human which comprises implanting hydrophilic biocompatible microparticles comprising (a) a positive charge and a cell adhesion promoter; and (b) autologous cells layered on the surface of the beads, into the urinary sphincter. The microparticles are preferably microspheres or microbeads as described herein. Further, the autologous cells are preferably taken from the area where the implantation is to be made. Serum or whole blood from the patient can be used to wash the microparticles prior to implantation. Implantation is preferably made using a syringe or other device suitable for the particular tissue of implantation.

In another embodiment, the invention encompasses a method of treating skin wrinkles in a human which comprises the administration or implantation of microparticles comprising a hydrophilic copolymer having a positive charge, and a cell adhesion promoter, which microparticles have been pre-treated with autologous cells. The microparticles can be simply exposed to the autologous cells or mixed thoroughly with autologous cells prior to implantation. The microspheres are preferably injected via syringe or other suitable device through a needle of 30 gauge or smaller into the area, or under the area, of the skin deficiencies.

In yet another embodiment, the invention encompasses the treatment or amelioration of skin wrinkles which comprises administering hydrophilic biocompatible microparticles comprising: (a) a positive charge and a cell adhesion promoter; and (b) autologous cells, collagen, collagen derivatives or glucosaminoglycans layered on the surface of the beads, into the area of or surrounding the skin wrinkles. In other words, microspheres or microbeads coated with a cell adhesion promoter and pre-treated with the appropriate tissue bulking cells, are administered to the area of treatment.

The present invention additionally provides methods of dermal augmentation and treatment of skin deficiency. Specifically, the invention provides a method of causing dermal augmentation in a mammal by administering a composition of elastic, hydrophilic, and substantially spherical microspheres in a biocompatible carrier to the mammal. The composition is injectable through a needle of about 30 gauge or smaller and the microspheres are not capable of being digested or eliminated by macrophage or other elements of the mammal's immune system. According to the present invention, a preferred method of administration is injecting the composition into an area of the subject mammal that is in need of dermal augmentation. A more preferred method of administration is injecting the composition into the subcutaneous layer of the subject mammal.

The dermal augmentation method of the present invention is especially suitable for the treatment of skin contour deficiencies, which are often caused by aging, environmental exposure, weight loss, child bearing, injury, surgery, in addition to diseases such as acne and cancer. Suitable for the treatment by the present invention's method are contour deficiencies such as frown lines, worry lines, wrinkles, crow's feet, marionette lines, stretch marks, and internal or external scars resulted from injury, wound, bite, surgery, or accident.

The invention also encompasses the use of the injectable compositions to treat skin deficiencies caused by diseases such as acne and cancer.

The present invention further provides a method of causing dermal augmentation in a mammal by administering the injectable suspension extracorporeally into organs, components of organs, or tissues prior to the inclusion of said tissues, organs, or components of organs into the body.

The invention further encompasses method for tissue bulking in a mammal by administering a composition of elastic, hydrophilic, non-toxic and substantially spherical microspheres in a biocompatible carrier to the mammal. The composition is injectable through needles of about 18 to about 26 gauge, preferably, 22 to 24 gauge, and preferably administered by injection directly into the site of treatment, e.g., the sphincter.

Thus, in one embodiment, the tissue bulking method is used for the treatment of gastroesophageal reflux disease in a mammal; preferably by direct administration via injection of the composition into the lower esophageal sphincter or the diaphragm of the mammal.

Similarly, the tissue bulking method is used for the treatment of urinary incontinence or urinary reflux disease via administration of the composition into the bladder sphincter or the urethra of the mammal.

The present invention further provides kit for performing dermal augmentation or tissue bulking. The kit comprises a syringe and a 30 gauge or smaller needle for dermal augmentation and an 18 to 26 gauge needle for tissue bulking. The syringe optionally comprises a composition of elastic, hydrophilic, non-toxic and substantially spherical microspheres in a biocompatible carrier. Alternatively, the syringe does not contain a solution or suspension but is accompanied by (a) dry sterilized microspheres which are ready for preparation of a suspension; (b) a preformed suspension of microspheres; and (c) dry microspheres and a biocompatible solution in separate containers. The final composition of microspheres is injectable through the needle into a mammal and the microspheres are not capable of being digested or eliminated through said mammal's macrophages or other elements of the immune system or the lymphatic system.

It should be recognized that both treatments for GERD, urinary incontinence, urinary reflux disease, and skin deficiencies described above can be used in combination with conventional therapies now used to treat these diseases or conditions, i.e., oral diuretics, antacids, suitable drug therapy, cosmetic surgeries and the like. Such combination therapy can lead to a faster, safer and more comfortable recovery for the patient.

As used herein the terms "administered", "implanted", or "implantation" are used interchangeably and mean that the material is delivered to the area of treatment by techniques know to those skilled in the art and appropriate for the disease to be treated. Both invasive and non-invasive methods may be used for delivery. "Injectable" as used in the present invention means capable of being administered, delivered or carried into the body via needle or other similar ways.

As used in the present invention, "microparticles" means polymer or combinations of polymers made into bodies of various sizes. The microparticles can be in any shape, although they are often in substantially spherical shape, in which case the microparticles are referred to as "microspheres" or "microbeads." Before injection or being composed into an injectable composition, the microspheres are sterilized. "Elastic" microparticles or microspheres refers to microparticles or microspheres comprise polymers that have elastic properties. Specific to the present invention, elastic microspheres means particles that are flexible enough so that they can be easily injected through needles of 18 gauge or smaller, yet the microspheres are not fragile so that they are not broken during the process of injection.

The microspheres of the present invention also comprise particles that are "hydrophilic," which, as used in the invention, means the particles can dissolve in, absorb, or mix easily with water or aqueous solution.

"Substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. The microspheres of the present invention may comprise, in addition to the particles, other materials as described and defined herein.

"Skin wrinkles," "skin deficiencies," and "skin contour deficiencies" are used interchangeable in the present invention to refer to skin conditions that are either abnormal or undesirable due to various internal or external conditions such as aging, environmental exposure to the sun and other elements, weight loss, child bearing, disease such as acne and cancer, surgery, wounds, accidents, bites, cuts.

"Dermal augmentation" in the context of the present invention refers to any change of the natural state of a mammal's skin and related areas due to external acts. The areas that may be changed by dermal augmentation include, but not limited to, epidermis, dermis, subcutaneous layer, fat, arrector pill muscle, hair shaft, sweat pore, and sebaceous gland.

"Tissue bulking" in the context of the present invention refers to any change of the natural state of a mammal's non-dermal soft tissues due to external acts or effects. The tissues encompassed by the invention include, but not limited to, muscle tissues, connective tissues, fats, and, nerve tissues. The tissues encompassed by the present invention may be part of many organs or body parts including, but not limited to, the sphincter, the bladder sphincter and urethra.

"Cell adhesion promoter" in the present invention means any material that, because of their presence in or association with the microspheres, promotes or enhances the adhesiveness of cells to the surface of the microspheres. These materials are often proteins that are bound to the surface of the microspheres through covalent bonds of the proteins and the polymers.

"Therapeutic agent" in the present invention refers to any substance that provides therapeutic effects or biological or physiological responses to the dermal augmentation or tissue bulking procedure. An example of therapeutic agent is an anti-inflammation agent that prevents or reduce the effect of inflammations associated dermal augmentation or tissue bulking procedure, an anti-inflammatory agent, an anti-bacterial agent, or an anti-histamine agent.

"Chemical modification" in the present invention means the changes of chemical properties and characteristics of the microspheres, either during their production process or by way of mixing or contacting them with various agents or tissues, such that the microspheres have the ability to perform, in addition to dermal augmentation or tissue bulking, other functions once injected into the body.

DETAILED DESCRIPTION OF THE INVENTION

The present invention provides a safe, effective, stable, and long lasting methods of tissue bulking and dermal augmentation, which methods are useful for the treatment of gastroesophageal reflux disease, urinary incontinence, urinary reflux disease, and skin deficiencies. The invention provides methods of tissue bulking and dermal augmentation by administrating injectable composition comprising elastic, hydrophilic, non-toxic and substantially spherical microspheres and a biocompatible carrier to a mammal in need of treatment for gastroesophageal reflux disease, urinary incontinence, urinary reflux disease, or skin deficiencies. The methods of the present invention are intended to encompass the following advantages: (1) the injected materials are not easily displaced within the tissues in which they were originally injected, thus the intended dermal augmentation or tissue bulking effect is achieved without repeated administration or causing adverse effects to the patient, (2) the injected materials are not readily digested, displaced, or eliminated either biochemically or through the immune or lymphatic system, thus the method is more effective and longer lasting, (3) the materials are of sufficient size to be injected through 18 to 26 gauge needles, preferably 22 to 24 gauge needles, for tissue bulking or 30 gauge or smaller needles for dermal augmentation, thus the method is more accurate, efficacious and less intrusive to the patient, (4) the injected particles are flexible, but not fragile, facilitating easy injection without being broken, thus providing easy and safe injection, and (5) the injected particles are not irregularly shaped and do not clump together, also providing easy and accurate injection. These benefits, whether alone or in combinations, enhance the effectiveness of the treatment and are safe, more convenient and comfortable for patients.

In one embodiment, the present invention uses microparticles, particularly microspheres or microbeads, having a positive charge on its surface and a cell adhesion promoter and optionally, a cell growth promoting agent, to treat GERD, urinary incontinence, and skin wrinkles. The microparticles of the invention are preferably used with autologous cells. In other words, the microparticles of the invention are colonized with the appropriate cells prior to implantation. This pre-implantation (pre-administration) step has been shown to reduce or eliminate immunological responses and implantation rejection reactions. Further, the use of non-biodegradable biologically compatible microbeads with positive charges and autologous cells, whether tissue-specific or not, improves tissue acceptance and overall treatment.

According to the methods of the present invention, treatment of GERD, urinary incontinence, and urinary reflux disease, and skin wrinkles is achievable while avoiding or substantially reducing adverse tissue reactions, including implantation rejection, degradation of particles, resorption, migration and other adverse events. The methods of the invention also involve increased connective tissue response.

Microbeads or microparticles for use in the present invention are based on a biocompatible, hydrophilic, substantially spherical, and non-toxic polymers. The microspheres are injectable through needle of 18 gauge or smaller and are not capable of being digested or eliminated through the mammal's immune or lymphatic system. The polymers may preferably be coated with agents which promote cell adhesion. Living cells may also attach to the microparticles forming layered cells therein which link with surrounding tissues to enhance long term stability of the beads.

Microparticles intended to be implanted, preferably through injection, in various locations of the body according to the present invention are composed of a non-resorbable hydrophilic polymer containing the appropriate material for cell adhesion, and may additionally contain radiopaque molecules or other marking agents, to facilitate localization by radiology prior to or during intervention. The microspheres of the present invention comprise elastomers, preferably elastomers selected from the group consisting of acrylic polymers, vinyl alcohol polymers, acrylate polymers, polysaccharides, silicones, or mixtures thereof. More preferably, the hydrophilic copolymers usable for this application are those of the acrylic family such as polyacrylamides and their derivatives, polyacrylates and their derivatives as well as polyallyl and polyvinyl compounds. All of these polymers are crosslinked so as to be stable and non-resorbable, and can contain within their structure other chemicals displaying particular properties, such as chemotactic effects, promotion of cell adhesion to cells or tissues, such as cells of the esophagus wall or the urethra wall, or skin cells, and/or marking agents.

The microparticles for use in the present invention are non-toxic to tissues and cells, biocompatible, and adhesive to various cells and tissues at the site of implantation by means of the cell growth they promote. In addition, these microparticles are non-resorbable and non-biodegradable, and thus are stable, durable, and will maintain their general shape and position once implanted at a desired site.

In general, microparticles for use in the present invention may have any shape, with microparticles which are substantially spherical in shape being preferred. Microparticles for use in the present invention may have diameters ranging between about 10 µm to about 1000 nm. Preferably, microparticles for use in the present invention which have cells adhered to the surface thereof will have diameters ranging between 50 µm and 1000 µm.

For purposes of tissue bulking, the microspheres of the invention preferably have diameters ranging from about 10 µm to about 500 nm, more preferably from about 100 µm to about 300 nm. For purposes of dermal augmentation, the microspheres preferably have diameters ranging from about 10 µm to about 400 µm, preferably from about 50 µm to about 200 µm.

Possible variations of the present invention include replacing the microparticles with any biocompatible, non-toxic non-resorbable polymeric particles, membrane, fibers or other solid substrates treated with an agent promoting cell adhesion. The invention also includes linear soluble polymers which, after injection, crosslink in situ to constitute a solid, cell adhesion promoting filling agent. Preparation and/or injection of empty microparticles (microbubbles) that are prepared in advance or are generated in place via the use of appropriate catheters, are also contemplated in this invention.

The microparticles, or other solid substrates, for use in the present invention are flexible, such that they can easily pass into and through injection devices and small catheters without being permanently altered, but the microparticles are also resistant to the muscle contraction stress generated during and after the implantation process. They are also thermally stable which allows for easy, convenient sterilization, and frozen storage.

The microparticles, or other solid substrates, for use in the present invention are also stable in suspension which allows the microparticles or other solid substrates to be formulated and stored in suspension and injected with different liquids. More specifically, the hydrophilic nature of the microparticles permits placing them in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like. Preferably, these injectable solutions contain microparticles or other solid substrates distributed approximately in caliber segments ranging between about 10 μm and about 2000 μm.

The microparticles of the present invention are both hydrophilic and cationic. The microparticles preferably comprise a copolymer of a neutral hydrophilic monomer, a difunctional monomer, one or more monomers having a cationic charge, and optionally, a functionalized monomer capable of rendering the microparticle detectable. The microparticles may also comprise one or more cell adhesion promoters and a marking agent.

The copolymer is preferably a hydrophilic acrylic copolymer which comprises in copolymerized form about 25 to about 98% neutral hydrophilic acrylic monomer by weight, about 2 to about 50% difunctional monomer by weight and about 0 to about 50% by weight of one or more monomers having a cationic charge.

By way of example, the copolymers described in French Patent 2,378,808, which is incorporated herein by reference, can be used in accordance with this invention to prepare the base microparticle copolymer.

As hydrophilic acrylic monomer, acrylamide and its derivatives, methacrylamide and its derivatives or hydroxymethylmethacrylate can be used.

Examples of difunctional monomer, include but are not limited to the N,N'-methylene-bis-acrylamide, N',N'-diallyltartiamide or glyoxal-bis-acrylamide.

Further, the monomer having a cationic charge, includes but is not limited to those carrying a tertiary or quaternary amine function, preferably diethylaminoethyl acrylamide, methacrylamidopropyl trimethylammonium or acrylamidoethyl triethylammonium.

In a particularly preferred embodiment, a copolymer comprising about 25 to about 98% methacrylamide by weight, about 2 to about 50% N,N-methylene-bis-acrylamide by weight is used.

In one particularly advantageous embodiment of the invention, it is possible to increase the stability of the microspheres by reticulating the adhesion agent. By way of example, in the case of gelatin, the reticulating agent can be chosen among the difunctional chemical agents reacting on the gelatin amines (e.g., glutaraldehyde, formaldehyde, glyoxal, and the like).

The functionalized monomer is generally obtained by chemical coupling of the monomer with a marker, which can be:

a chemical dye, such as Cibacron Blue or Procion Red HE-3B, making possible a direct visualization of the microspheres (Boschetti, *J. Biochem-Biophys. Meth.*, 19:21-36 (1989)). Examples of functionalized monomer usable for this type of marking N-acryloyl hexamethylene Cibacrone Blue or N-acryloyl hexamethylene Procion Red HE-3B;

a magnetic resonance imaging agent (erbium, gadolinium or magnetite);

a contrasting agent, such as barium or iodine salts, (including for example acylamino-e-propion-amido)-3-triiodo-2,4,6-benzoic acid, which can be prepared under the conditions described by Boschetti et al. (*Bull. Soc. Chim., No. 4 France*, (1986)). In the case of barium or magnetite salts, they can be directly introduced in powered form in the initial monomer solution.

As indicated above it is also possible to mark the microspheres after their synthesis. This can be done, for example, by grafting of fluorescent markers derivatives (including for example fluorescein isothiocyanate (FITC), rhodamine isothiocyanate (RITC) and the like).

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), or any other natural or synthetic biological cell adhesion agent.

Preferably, the cell adhesion promoter is present in the microparticle, or other solid substrate, in an amount between about 0.1 to 1 g per ml of settled microparticles.

Microparticles are prepared by suspension polymerization, drop-by-drop polymerization or any other method known to the skilled artisan. The mode of microparticle preparation selected will usually depend upon the desired characteristics, such as microparticle diameter and chemical composition, for the resulting microparticles. The microparticles of the present invention can be made by standard methods of polymerization described in the art (see, e.g., E. Boschetti, *Microspheres for Biochromatography and Biomedical Applications. Part I, Preparation of Microbands* in: Microspheres, Microencapsulation and Liposomes, John Wiley & Sons, Arshady R., Ed., vol. 2, p 171-199 (1999), which is incorporated herein by reference). Microspheres are prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

Cell adhesion promoters or marking agents are introduced on microbeads by chemical coupling procedures well known in affinity chromatography, referred to by the term "ligand immobilization". Another method of introduction is by diffusion within the gel network that constitutes the bead and then trapping the diffused molecules in place by precipitation or chemical cross-linking. Therapeutic agents, drugs or any other active molecules that are suitable for transportation by the beads can also be introduced into the microbeads prior to bead implantation according to this last method.

The microspheres of the present invention also can be chemically modified so that they will "carry" therapeutic effects, vascularization effects, anti-vascularization effects, visualization properties, anti-inflammatory effects, anti-bacterial effects, or anti-histamine effects, or combinations thereof. The chemical modification of the microspheres of the present invention is made possible by the fact that the microspheres comprise particles made of polymers that are crosslinked so that they can contain chemicals within their structures that possess various properties and that they possess unique characteristics associated with surface covalent bonds. The chemical modification of the microspheres of the present invention may also occur through the interactions between the microspheres and the neighboring cells and tissue after the administration.

The microspheres of the invention can also be obtained by standard methods of polymerization described in the art such as French Patent 2,378,808 and U.S. Pat. No. 5,648,100, each of which is incorporated herein by reference. In general, the polymerization of monomers in solution is carried out at a temperature ranging between about 0° C. and about 100° C. and between about 40° C. and about 60° C., in the presence of a polymerization reaction initiator.

The polymerization initiator is advantageously chosen among the redox systems. Notably, it is possible to use combinations of an alkali metal persulfate with N,N,N',N'-tetramethylethylenediamine or with dimethylaminopropionitrile, organic peroxides such as benzoyl peroxides or even 2,2'-azobis-isobutyronitrile.

The quantity of initiator used is adapted by one skilled in the art to the quantity of monomers and the rate of polymerization sought.

Polymerization can be carried out in mass or in emulsion.

In the case of a mass polymerization, the aqueous solution containing the different dissolved constituents and the initiator undergoes polymerization in an homogeneous medium. This makes it possible to access a lump of aqueous gel which can then be separated into microspheres, by passing, for example, through the mesh of a screen.

Emulsion or suspension polymerization is the preferred method of preparation, since it makes it possible to access directly microspheres of a desired size. It can be conducted as follows: The aqueous solution containing the different dissolved constituents (e.g., different monomers, cell adhesion agent), is mixed by stirring, with a liquid organic phase which is not miscible in water, and optionally in the presence of an emulsifier. The rate of stirring is adjusted so as to obtain an aqueous phase emulsion in the organic phase forming drops of desired diameter. Polymerization is then started off by addition of the initiator. It is accompanied by an exothermic reaction and its development can then be followed by measuring the temperature of the reaction medium.

It is possible to use as organic phase vegetable or mineral oils, certain petroleum distillation products, chlorinated hydrocarbons or a mixture of these different solutions. Furthermore, when the polymerization initiator includes several components (redox system), it is possible to add one of them in the aqueous phase before emulsification.

The microspheres thus obtained can then be recovered by cooling, decanting and filtration. They are then separated by size category and washed to eliminate any trace of secondary product.

The polymerization stage can be followed by a stage of reticulation of the cell adhesion agent and possibly by a marking agent stage in the case of microspheres rendered identifiable by grafting after synthesis.

Microparticles of the present invention which have the specific properties of cell adhesion and growth promotion can be used directly for tissue bulking or dermal augmentation. Moreover, the microparticles of the present invention can have specific autologous cells grown on their surface in vitro, thereby making the microparticles particularly useful for tissue bulking or dermal augmentation.

Prior to the present invention, the injection of implantable substances suspended in a physiological solution into a tissue resulted in the formation of discrete aggregates inside the muscle mass. These discrete aggregates can constitute various amounts of the implanted substance which stays together, however, the substance does not become attached to or a part of the tissue itself. This detachment allows the implanted substance to move from the original implantation site.

According to the present invention, in order to avoid this problem, the microparticles may be injected individually and separately, or more preferably, the surface of the microparticles may be colonized by a layer of cells for better integration and long term stability of the implant.

Microparticles of the present invention demonstrate superior ability to grow cells on their surfaces. For example, primary muscle cells have been successfully adhered to the surface of the microparticles of the present invention thereby allowing for a better integration within a muscle tissue. In addition, since the ultimate goal of tissue bulking is to artificially increase tissue mass, preadipocytes have also been used to colonize the surface of the microparticles prior injection. In this case, the preadipocytes have a volume similar to any other regular cell, but after implantation when the preadipocytes are subject to in vivo physiological conditions, they accumulate droplets of fats thereby increasing the mass of the implant by more than 10% in volume.

The present invention provides a method for causing tissue bulking in a mammal. The method comprises administering a composition of elastic, hydrophilic, non-toxic and substantially spherical microspheres in a biocompatible carrier to the mammal. The composition is injectable through a needle of about 18 to about 26 gauge and the microspheres are not capable of being digested or eliminated by macrophage or other elements of said mammal's lymphatic system. The tissue bulking method of the present invention is suitable for the treatment of various tissue defects including, but not limited to, dental tissue defects, vocal cord tissue defects, or other non-dermal soft tissue defects. The present method is particularly suitable for GERD, urinary incontinence, or urinary reflux disease.

The injection method of the present invention can be carried out by any type of sterile needles of 18 gauge or smaller and corresponding syringes or other means for injection, such as a three-way syringe. The injection is preferably made into the area that needs tissue bulking treatment. The needles, syringes and other means for injection are commercially available from suppliers such as VWR Scientific Products (West Chester, Pa.), Becton Dickinson, Kendal, and Baxter Healthcare. The size of the syringe and the length of the needle used will dependent on the particular injection based on factors such as the specific disease or disorders being treated, the location and depth of the injection, and the volume and specific composition of the injectable suspension being used. A skilled practitioner will be able to make the selection of syringe and needle based on experience and the teaching of the present invention.

The present invention additionally provides a kit for performing dermal augmentation tissue bulking. The kit comprises an 18 gauge or smaller needle and a corresponding syringe (both of which are sterile), wherein the syringe optionally contains a composition comprising biocompatible, elastic, hydrophilic, non-toxic and substantially spherical microspheres and a biocompatible carrier. The composition is injectable through the needle and the microspheres are not capable of being eliminated by macrophage or other elements of said mammal's immune or lymphatic system. Alternatively, the kit comprises an 18 gauge or smaller needle, a corresponding syringe, and separate containers containing the microspheres in dried and sterilized form and the biocompatible solvent. The dried sterilized microspheres and the solvent are ready to be mixed for injection either in their respective containers or in the syringe. These kits are sterile and ready to use. The kits are designed in various forms based the sizes of the syringe and the needles and the volume of the injectable composition contained therein, which in turn are based on the specific skin or tissue defects the kits are designed to treat.

According to the present invention, one means of performing tissue bulking in a patient can be described as follows:
a) Primary cells are extracted from the patient by a simple biopsy and isolated;
b) These cells are grown on the surface of the microparticles under growth promoting conditions (e.g., possibly using a nutrient media which contains autologous serum (drawn from the patient), until confluence);
c) The microparticles having the patient's cells grown on the top are injected into the patient's target tissue to be bulked.

For the treatment of GERD, the microparticles, or other solid substrates, are preferably introduced via the esophagus, either by endoscopic delivery or by laparoscopic technique, and are injected into the walls of the sphincter where the esophagus meets the stomach, i.e., the lower esophageal sphincter. This decreases the internal lumen of the sphincter muscle thus permitting easier contraction of the muscle with reduced regurgitation of the gastric fluids into the esophagus. In addition, this treatment reduces the inflammation of the lower esophagus. The microparticles, or other solid substrates, may also be loaded with X-ray opaque dye or other imaging agents for subsequent X-ray visualization.

In another embodiment, microparticles injected into the sphincter at the junction of the esophagus and stomach in order to treat GERD may also include an amount of a drug used to treat GERD, such as $H_2$ histamine antagonists including cimetidine, ranitidine, famotidine and nizatidine; inhibitors of $H^+,K^+$-ATPase including omeprazole and lansoprazole; antacids including e.g., $Al(OH)_3$, $Mg(OH)_2$, and $CaCO_3$. As with the treatment of urinary incontinence, urinary reflux disease, and skin wrinkles, the microspheres may also be used with anti-inflammatory agents, angiogenesis inhibitors, radioactive elements, and antimitotic agents.

Other therapeutic agents to be used in combination with the microspheres or microparticles of the present invention include those for the treatment of skin disorders, GERD, urinary incontinence and urinary reflux disease as reported in Goodman & Gilman's The Pharmacological Basis of Therapeutics, 9th Ed., McGraw-Hill (1996) and The Physicians's Desk Reference® 2000.

The primary advantages of the method of treating GERD according to the present invention over the prior art methods are:
a) Less invasive effects on the patient compared to surgery;
b) More accurate and effective delivery of the microspheres and therapeutic agents;
c) More permanent effects over antacids or other drugs;
d) Good biocompatibility with chemotactic effects; and
e) Ability to use X-ray visualization or MRI to assist in follow-up evaluation of the patient.

For the treatment of urinary incontinence and urinary reflux disease, the microparticles or microspheres of the present invention are injectable through needles of about 18 gauge to about 26 gauge, preferably, 22 to 24 gauge, and are not capable of being eliminated through the lymphatic system. The microparticles are introduced via the urethra and injected into the walls of the bladder sphincter, decreasing the internal lumen of the sphincter muscle thus permitting easier contraction of the muscle with reduced likelihood of incontinence. The microparticles, or other solid substrate, may also be loaded with X-ray opaque dye, or other imaging agents for subsequent X-ray visualization.

In another embodiment, microparticles injected into the bladder sphincter in order to treat urinary incontinence or urinary reflux disease may also include an amount of a drug used to treat urinary incontinence or urinary reflux disease, such as antidiuretics, anticholinergics, oxybutynin and vasopressins.

Injected microparticles can generate some transient adverse reactions such as local inflammation, therefore the microparticles can contain or be injected with anti-inflammatory drugs, such as salicylic acid derivatives including aspirin; para-aminophenol derivatives including acetaminophen; non-steroidal anti-inflammatory agents including indomethacin, sulindac, etodolac, tolmetin, diclodfenac, ketorolac, ibuprofen, naproxen, flurbiprofen, ketoprofen, fenoprofen, oxaprozin; anthranilic acids including mefenamic acid, meclofenamic acid; enolic acids such as piroxicam, tenoxicam, phenylbutazone, oxyphenthatrarone; nabumetone; VIOXX (rofecoxib) and CELEBREX (celecoxib). These anti-inflammatories are preferably adsorbed on the microparticle's network and released slowly over a short period of time (a few days). The microparticles may also be used to release other specific drugs which can be incorporated within the microparticle network before injection into the patient. The drug would be released locally at the site of implantation over a short period of time to improve the overall treatment.

Incorporation of active molecules, such as drugs, into the microparticles of the present invention can be accomplished by mixing dry microparticles with solutions of said active molecules or drugs in an aqueous or hydro-organic solution. The microparticles swell by adsorbing the solutions and incorporate the active molecule of interest into the microparticle network. The active molecules will remain inside the microparticle due to an active mechanism of adsorption essentially based on ion exchange effect. The microparticles by their nature carry cationic groups and have the ability to adsorb anionic molecules, such as well known anti-inflammatory drugs, and these anionic molecules are then released slowly upon injection into the patient due to the action of physiological salt and pH. The ability of various types of microparticles to adsorb drug molecules may be readily determined by the skilled artisan, and is dependent on the amount of cationic monomers present in the initial solution from which the microparticles are prepared.

Some of the primary advantages of treating urinary incontinence or urinary reflux disease according to the present invention over prior art methods are:
a) More permanent effect than the use of regular viscous solutions of collagen;
b) More accurate and effective delivery of the microspheres and therapeutic agents;
c) Good biocompatibility with chemotactic effect;
d) Visualization under X-ray or MRI to assist in follow-up evaluation; and
e) Preventing repeated treatments with resorbable naturally occurring substances like collagen.

The primary advantages of the method of treating skin wrinkles according to the present invention are:
a) less invasive effects on the patient compared to surgery;
b) more accurate and effective delivery of the microspheres and therapeutic agents;
c) more permanent effects than the use of collagen injections; and
d) good biocompatibility with chemotactic effects.

The dermal augmentation method of the present invention comprises administering a composition of elastic, hydrophilic, non-toxic and substantially spherical microspheres in a biocompatible carrier to a mammal in need of such treatment. The composition is injectable through needles of about 30 gauge or smaller and the microspheres are not capable of being digested or eliminated through macrophages or other elements of the immune system. The injectable composition is preferably a suspension of the microspheres in the biocompatible carrier. The microspheres are preferably injected into the mammal's subcutaneous layer. The microparticles may also include one or more anti-inflammatory agents.

Suitable for treatment using the dermal augmentation method of the present invention are skin contour deficiencies caused by various conditions including, but not limited to, aging, environmental exposure, weight loss, child bearing, surgery, disease such as acne and cancer, or combinations thereof. The dermal augmentation method of the present invention is particularly suitable for skin contour deficiencies such as frown lines, worry lines, wrinkles, crow's feet, facial scars, marionette lines, stretch marks, surgical scars, wounds, and cuts and bites due to injury or accidents.

The present invention also provides methods of causing tissue bulking or dermal augmentation by injecting the injectable composition not directly into the body, but extracorporeally into organs, components of organs, or tissues prior to their inclusion into the body, organs, or components of organs.

The injection of the present invention's method can be preferably carried out by any type of sterile syringes with needles of about 18 to 26 gauge. The size of the syringe and the length of the needle used will dependent on the particular injection based on factors such as the specific disease or disorders being treated, the location and depth of the injection, and the volume and specific composition of the injectable suspension being used. A skilled practitioner will be able to make the selection of syringe and needle based on experience and the teaching of the present invention.

In some embodiments of sphincter bulking, beads are coated and injected under physiological conditions into the sphincter. The sphincter volume increases proportionally to the amount of injected beads and the lumen size decreases. The beads are progressively and non-reversibly integrated within the muscles.

The invention is further defined by reference to the following examples that describe in detail the preparation of microparticles for use in tissue bulking, and the treatment of skin wrinkles, urinary incontinence, and GERD. The following examples are illustrative only and should in no way limit the scope of the present invention. It will be apparent to those skilled in the art that many modifications, both to materials and methods, may be practiced without departing from the purpose and scope of this invention.

EXAMPLES

Example 1

Preparation of Irregular Hydrogel Particles with Chemotactic Properties 58 grams of sodium chloride and 27 grams of sodium acetate were dissolved at room temperature in 100 ml of demineralized water. To this solution 400 ml of glycerol were added, the pH was adjusted to 6.0 and monomers were then dissolved. More specifically to this solution 90 gram of methylolacrylamide, 2 g of methacrylamidopropyl-trimethyl-ammonium-chloride hydrochloride and 10 gram of N,N'-methylene-bis-acrylamide were added and the mixture was agitated until complete solubilization. The solution was heated at about 70° C. and 100 ml of a solution of gelatin at a concentration of 500 mg/ml was added. The total volume of the mixture was then adjusted to 1000 ml by addition of demineralized water. Finally 20 ml of 70 mg/ml ammonium persulfate aqueous solution and 4 ml of N,N,N',N'-tetramethyl-ethylene-diamine was added. The obtained mixture was stored at 70° C. for about 3 hours until formation of a compact three-dimensional gel. This gel was totally insoluble in water. It was cut in small pieces and then ground to get very small particles of a dimension close to 100-200 μm. The particles were then suspended in 1 liter of physiological buffer containing 5% (w/v) glutaraldehyde and were shaken for two hours. Finally the particles were extensively washed to eliminate unpolymerized material, by-products and salts. To obtain homogeneous particle size distribution the particle suspension was sieved using an appropriate sieving net.

These particles possess the characteristics desired for tissue cell adhesion prior to muscle bulking and include cationic groups and adhesion agents for an effective cell adhesion mechanism.

Example 2

Preparation of Spherical Polyacrylic Hydrogel Gel Particles with Chemotactic Properties The solution of monomers prepared as described in Example 1 above was poured slowly into 1500 ml of stirred and hot paraffin oil (50-70° C.). After a few minutes a suspension/emulsion of liquids was obtained (the aqueous monomer solution was dispersed into oil and forms very small spherical droplets) and the polymerization occurred in suspension. The microdroplets were transformed into microbeads. The solid microbeads were recovered by centrifugation and suspended in 1 liter of physiological buffer containing 5% (w/v) glutaraldehyde and shaken for two hours. Finally the particles were extensively washed with water to eliminate completely the oil traces. Organic solvent extraction can be used for a more effective oil removal or an extensive washing in the presence of traces of nonionic detergents. The obtained microbeads are calibrated if necessary by sieving through a nylon net and sterilized in an autoclave. These microspheres possess desired characteristics and properties for cell adhesion prior to muscle bulking.

Example 3

Preparation of Hydrophilic Spherical Polystyrene Copolymer Particles Useful for Tissue Bulking 10 gram of styrene is mixed with 60 ml of toluene. 1 gram of divinylbenzene, 1 gram of dimethyl-aminoethyl-methacrylate and 1 gram of dimethyl-acrylamide are added to the resulting solution. After complete solubilization the monomer solution is mixed with 1% of AIBN (2,2'-azobisisobutyronitrile) as a polymerization catalyst and with 40 ml of paraffin oil as a viscosity inducer agent. The mixture is poured in an agitated water solution containing 0.5% Tween 80. In this situation there is formation of droplet suspension which turns into solid microbeads when the temperature is raised to 80-90° C. for three to five hours. The resulting beads are dried and organic solvents extracted. They are then swollen in an aqueous solution of collagen in phosphate buffer at neutral pH. Embedded collagen is then crosslinked with glutaraldehyde as described in Examples 1 and 2. The resulting beads possess cationic charges to interact with cell tissues and collagen for cell adhesion, and a chemotactic agent for cell growth and biocompatibility. They are suitable as tissue bulking agent.

Example 4

Preparation of Hydrophilic Silicone Beads for Cell Adhesion and Tissue Bulking 10 gram of silicone beads of a diameter of 20-300 μm are suspended in 30 ml of a solution of hexadecylamine (10 mg/ml) in ethylacetate. The suspension is stirred for two hours and 100 ml of ethanol is added. A 1 M ammonium sulfate or sodium chloride solution in water is added slowly until a 300 ml suspension is obtained. The amino-containing silicone beads are then reacted with a butanedioldiglycydylether in alkaline conditions. Epoxy derivatives are thus obtained on which gelatin is coupled using a method well known in the art. The resulting beads have the target properties of biocompatibility, hydrophilicity, non-biodegradability and cell adhesion by the presence of cationic amino groups and of gelatin as a cell growth promoting agent. They are suitable for tissue bulking in accordance with the present invention.

Example 5

Preparation of Beads for Tissue Bulking Containing Adhesion Factors

Beads prepared according to Example 2 were chemically activated with well known reagents used in the preparation of affinity chromatography sorbents. Activated beads were then used for the immobilization of cell adhesion agents such as fibronectin or vitronectin or laminin. Adhesion agents were dissolved at 1-10 mg/ml in a coupling buffer (100 mM carbonate or borate buffer pH 8 to 10) and the solution was mixed with the activated beads. The resulting beads possess the target properties of cell adhesion and growth, non-biodegradability and were non-resorbable. They are suitable for cell adhesion and permanent tissue bulking in accordance with the present invention. Similarly, beads prepared according to Examples 3 and 4 can also be used.

Example 6

Preparation of Spherical Polyacrylic Hydrogel Particles with Chemotactic Properties Microbeads commercially available under the name SPEC-70 (BioSepra Inc., Marlborough, Mass.) are polyacrylic polyanionic beads with elastic properties suitable for tissue bulking applications. However, these microbeads are not chemotactic and do not possess cationic charges. SPEC-70 microbeads are first drained under vacuum to eliminate water and then suspended in an aqueous solution of 1% chondroitin sulfate sodium salt in physiological conditions. Once this compound is absorbed on the bead structure, the beads are drained under vacuum and suspended in an aqueous solution containing 20% polylysine by weight. The suspension is shaken for a few hours and then drained under vacuum and rapidly washed with distilled water. The beads are then suspended in a solution of 5% butanedioldiglycidylether in ethanol and shaken overnight. Under these conditions, the polylysine is crosslinked as well as chondroitin sulfate. The resulting modified beads possess properties such as cationic charge for cell adhesion and promoting agents for cell growth such as polylysine and chondroitin sulfate.

Example 7

Preparation of Radiopaque Microbeads with Chemotactic Properties for Tissue Bulking Microbeads from Examples 2 were drained under vacuum and then suspended in a saturated solution of barium chloride. They were shaken for two hours at room temperature and then drained under vacuum to eliminate the excess of barium chloride solution. The beads were suspended in a saturated solution of ammonium sulfate and shaken for two additional hours before elimination of the excess ammonium sulfate by vacuum filtration. This operation of contact with barium salts and ammonium sulfate can be repeated several times until the resulting radiopaque precipitate inside the beads reaches the desired amount. Resulting beads have radiopaque properties without having lost their initial desirable properties for tissue bulking. The microbeads from Examples 3, 4 and 6 can be similarly used.

Example 8

Preparation of Radiopaque Microbeads with Chemotactic Properties for Tissue Bulking Microbeads from Example 6 coated with polylysine are washed extensively with distilled water and suspended in a solution of sodium triazoate. The suspension pH is adjusted at about 7 by addition of acetic acid and shaken for several hours. The triazoate which is a radiopaque molecule is adsorbed tightly to the beads and the remaining reagents are eliminated by washing under vacuum. The resulting beads still possess cell promotion properties and now radiopacity as well.

Example 9

Introduction of Anti-Inflammatory Drugs Inside the Bulking Beads

Microbeads described in the previous Examples may generate local temporary inflammatory reactions when injected in the target tissue. To avoid or decrease this phenomenon, the microbeads once coated with autologous cells can be filled with one or more anti-inflammatory drugs. The microbeads are cationic by their nature and can absorb anionic drugs by ion exchange effect.

Prior to injection microbeads are mixed with a 10 mg/ml anti-inflammatory anionic drug solution in sterile physiological saline. The suspension is shaken for several hours, and the beads filled with the drug are recovered by filtration or centrifugation. The resulting anti-inflammatory containing microbeads may then be used as tissue bulking agents for use in the present invention.

Example 10

In Vitro Pre-Adipocytes Adhesion and Growth on Polymeric Beads

In order to assess the ability of polymeric beads from Example 2 to allow adhesion and growth of pre-adipocytes, fresh pre-adipocytes were collected and isolated from Wistar rat peri-epididymal fat tissue. Pre-adipocytes were then cultured in the presence of above described microbeads at a concentration of about $7.1\times10^5$ to about $1.7\times10^6$ cells/ml using the classical protocol for microcarrier culture in vitro. In a first phase the cells adhere on the bead surface and then they grow to totally cover the bead surface. The total colonization period is about 72 hours.

Pre-adipocytes from this type of culture show good growth and specific biological activity associated with differentiation into adipocytes (accumulation of lipids). Moreover these cells show the presence of specific enzymatic markers such as glycerol-3-phosphate-dehydrogenase and malate dehydrogenase. Microbeads having cells adhered thereto are useful for tissue bulking for use in the present invention. The polymeric beads of Examples 2 to 5 can be similarly assessed.

Example 11

Culture of Pre-Adipocytes and Myocytes on Microbeads In Vitro to Check their Ability of Integrate into an In Vivo Tissue Preadipocytes and smooth muscle cells were isolated from Wistar rats according to a classical protocol to eliminate most of other contaminating cells. Separately these cells were cultured in a Petri dish in the presence of Dulbecco's Modified Eagle Medium supplemented with 10% fetal bovine serum. Gelatin-coated cationic microbeads prepared in accordance with Example 2 were added to cells cultured in vitro until they covered the surface of the Petri dish. Initial cell seed concentration was $0.7\times10^6$ cells/ml.

Repeated observations showed that cells adhered on the surface of microbeads and further multiplied to cover all the surface of the beads. After 5 to 7 days of culturing, there was formation of a solid network of beads where cells acted as a binder to consolidate the blocks of several beads. In most cases there were formation of solid non dissociable aggregates comprising beads and cells.

When, after a growing period (generally 5 to 7 days), a differentiating element such as 3,3',5-triiodo-D-thyronine was added to preadipocytes, the preadipocytes started to accumulate fats as micro-droplets within the cytoplasm.

Specific staining with 3,3'-dioctadecyloxacarbocyanine perchlorate or 2'-[4-hydroxyphenyl]-5-[4-methyl-1-piperazinyl]2,5'-bi-1H-benzimidazole demonstrated good adhesion of the cells on the bead substrate.

Staining of the cells with red oil at the beginning of the differentiating phase evidenced the accumulation of fats inside the cells.

In addition, specific enzymatic reactions of malic enzyme indicated that, at the end of the culture, resulting adipocytes were functionally viable with their major expressed characteristics. This enzyme is not expressed at the beginning of the culture and appeared simultaneously with the accumulation of fats.

Smooth muscle cells were also followed in their proliferation by DNA synthesis assay; their adhesion on the substrate was followed as per preadipocyte cells. Myocytes also showed good proliferation as well as adhesion on the beads.

Example 12

In Vitro Myocyte Adhesion and Growth on Polymeric Beads

In order to assess the ability of polymeric beads from Example 2 to allow adhesion and growth of muscle cells, fresh smooth cell myocytes were collected from rat esophagus according to classical procedures. Cells were then cultured in the presence of above described microbeads at a concentration of about $10^6$ cells/ml using the classical protocol for microcarrier culture in vitro. In a first phase the cells adhered on the bead surface and then they grow until they cover the total bead surface. The total colonization period was about 72 hours.

Myocytes from this type of culture showed good growth and behavior and displayed the specific myosin marker. These microbeads having cells adhered thereto are useful for tissue bulking in accordance with the present invention. The beads from Examples 2 to 5 can be similarly assessed.

Example 13

Preparation of Injectable Suspension of Cell-Microbead Particles for In Vivo Bulking At the issue of cell culture phase, the cell-bead particles are collected by filtration and washed extensively with blood serum from the host where the material is to be implanted. This operation ensures the elimination of foreign material from cell culture. The microbeads are then suspended in a few ml of autologous serum (a ratio of beads/serum is about 1:1) and are ready to be injected within the tissue to be bulked by means of an appropriate syringe or other injection device.

Example 14

Preparation of Injectable Suspension of Cell-Microbeads Particles for In Vivo Bulking Microbeads described in Example 2 are colonized with rat muscle cells according to Example 10 and conditioned according to Example 13 using rat serum diluted with physiological saline (50%-50%). The final sterile suspension of cells anchored on beads (50% of volume is constituted of beads and 50% of physiological saline) is injected in the right thigh muscle of a rat. Three months after bead injection the muscle was observed in its shape and histologically examined. Muscle volume should be larger than the left thigh muscle upon autopsy. Beads inside the muscle mass should appear surrounded by fibroblastic cells with no specific adverse inflammatory or necrosis effects.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

Other embodiments are within the following claims.

What is claimed:

1. A method for dermal augmentation in a mammal comprising injecting a composition of non-biodegradable, elastic, hydrophilic, non-toxic and substantially spherical microspheres having a diameter of from about 10 µm to about 400 µm in a biocompatible carrier to said mammal through a needle of about 30 gauge or smaller, wherein the microspheres comprise one or more of: acrylamide polymers, vinyl alcohol polymers, or derivatives and mixtures thereof.

2. The method of claim 1, wherein the composition is a suspension of said microspheres in said biocompatible carrier.

3. The method of claim 1, wherein there is no aggregation or clumping of the microspheres prior to or during the administration.

4. The method of claim 1, wherein the composition further comprises a therapeutic agent, radio-pacifying agent, contrast media, or mixtures thereof.

5. The method of claim 4, wherein said therapeutic agent is bound to the microspheres.

6. The method of claim 1, wherein the microspheres are capable of being chemically modified to have therapeutic effects, anti-inflammatory effects, anti-bacterial effects, anti-histamine effects, or combinations thereof.

7. The method of claim 6, wherein the chemical modification of the microspheres is caused by interactions between the microspheres and neighboring tissues after administration thereof.

8. The method of claim 1, wherein the administration comprises injecting said composition into an area of said mammal in need of dermal augmentation.

9. The method of claim 8, wherein the administration comprises injecting said composition into the subcutaneous layer.

10. The method of claim 1, wherein the dermal augmentation is for treatment of contour deficiencies of said mammal.

11. The method of claim 10, wherein the contour deficiencies are caused by aging, environmental exposure, weight loss, child bearing, surgery, disease, or combinations thereof.

12. The method of claim 11, wherein the disease is acne, skin cancer, or combination thereof.

13. The method of claim 11, wherein the contour deficiencies are one or more of the group consisting of frown lines, worry lines, wrinkles, crow's feet, marionette lines, stretch marks, and internal or external scars resulted from injury, wound, surgery, bites, cuts, or accident.

14. The method of claim 1, wherein the mammal is human.

15. The method of claim 1, wherein the administration comprises injecting said composition extracorporeally into organs, components of organs, or tissues prior to their inclusion into said mammal's body, organs, or components of organs.

* * * * *

UNITED STATES PATENT AND TRADEMARK OFFICE
CERTIFICATE OF CORRECTION

PATENT NO. : 9,205,053 B2  
APPLICATION NO. : 12/534070  
DATED : December 8, 2015  
INVENTOR(S) : Jean-Marie Vogel et al.

Page 1 of 1

It is certified that error appears in the above-identified patent and that said Letters Patent is hereby corrected as shown below:

Claims

Column 24, Claim 12, Line 7, reads, ". . . cancer, or combination thereof." which should read ". . . cancer, or combinations thereof."

Column 24, Claim 13, Line 11, reads, ". . . external scars resulted from injury, . . ." which should read ". . . external scars resulting from injury, . . ."

Signed and Sealed this  
Seventh Day of June, 2016

Michelle K. Lee  
*Director of the United States Patent and Trademark Office*